(12) United States Patent
Aiba et al.

(10) Patent No.: US 9,133,446 B2
(45) Date of Patent: Sep. 15, 2015

(54) ALKALINE PHOSPHATASE

(71) Applicant: TOYOBO CO., LTD., Osaka-shi, Osaka (JP)

(72) Inventors: Hiroshi Aiba, Tsuruga (JP); Takahide Kishimoto, Tsuruga (JP); Yoshiaki Nishiya, Tsuruga (JP)

(73) Assignee: TOYOBO CO., LTD., Osaka (JP)

( * ) Notice: Subject to any disclaimer, the term of this patent is extended or adjusted under 35 U.S.C. 154(b) by 0 days.

(21) Appl. No.: 13/973,557

(22) Filed: Aug. 22, 2013

(65) Prior Publication Data

US 2014/0030790 A1 Jan. 30, 2014

Related U.S. Application Data

(63) Continuation-in-part of application No. PCT/JP2012/053924, filed on Feb. 20, 2012.

(30) Foreign Application Priority Data

Feb. 23, 2011 (JP) .................................. 2011-036954

(51) Int. Cl.
*C12N 9/16* (2006.01)

(52) U.S. Cl.
CPC ........... *C12N 9/16* (2013.01); *C12Y 301/03001* (2013.01)

(58) Field of Classification Search
CPC .............................................. C12Y 301/03001
USPC .............................................. 424/94.6; 435/8
See application file for complete search history.

(56) References Cited

FOREIGN PATENT DOCUMENTS

| JP | 2002-360259 A | 12/2002 |
|---|---|---|
| JP | 3507890 B2 | 3/2004 |
| JP | 4035738 B2 | 1/2008 |

OTHER PUBLICATIONS

Database DDBJ/EMBL/Genbank [online], Accession No. CP000563, Region: 4148666 . . . 4149943, <http://www.ncbi.nlm.nih.gov/nuccore/125995462?sat=14&satkey=5349874> Dec. 8, 2010 updated, [retrived on May 1, 2012] Copeland A. et al., Definition: *Shewanella baltica* OS155, complete genome.
Database DDBJ/EMBL/Genbank [online], Accession No. CP000503, Region: 872197..873519, <http://www.ncbi.nlm.nih.gov/nuccore/230556926?sat=14&satkey=5351581> Dec. 10, 2010 updated, [retrieved on May 1, 2012] Copeland A. et al., Definition: *Shewanella* sp. W3-18-1, complete genome.
Database DDBJ/EMBL/Genbank [online], Accession No. CP000681, Region: 3681878..3683200, <http://www.ncbi.nlm.nih.gov/nuccore/145562801?sat=14&satkey=5440579> Dec. 8, 2010 updated, [retrieved on May 1, 2012] Copeland A. et al., Definition: *Shewanella purefaciens* CN-32, complete genome.
Suzuki, Yutaka et al., "Gene Cloning, Overproduction, and Characterization of Thermolabile Alkaline Phosphatase from a Psychrotrophic Bacterium", Japan, 2005, vol. 69, No. 2, pp. 364-373.
Chang, Ho-Won et al., "*Shewanella basaltis* sp. nov., a marine bacterium isolated from black sand", International Journal of Systematic and Evolutionary Microbiology, 2008, vol. 58, No. 8, pp. 1907-1910.
Murakawa, Takeshi et al., "Cloning of Cold-active Alkaline Phosphatase Gene of a Psychrophile, *Shewanella* sp., and Expression of the Recombinant Enzyme", Bioscience, Biotechnology, and Biochemistry, Japan, 2002, vol. 66 No. 4, pp. 754-761.
International Search Report dated May 22, 2012, issued in corresponding application No. PCT/JP2012/053924.
A. Copeland et al., "*Shewanella baltica* OS155, complete genome", Databest DDBJ/EMBL/Genbank [online], Accession No. CP000563, Region: 4148666..4149943, <http://www.genome.gov/page.cfm?pageID=10506376> Jan. 28, 2014 updated, cited in Chinese Office Action dated Aug. 27, 2014, issued in corresponding Chinese Patent Application.
Extended European Search Report dated Oct. 24, 2014, issued in corresponding EP application No. 12749697.4 (6 pages).
E. Yu Plisova et al., "A Highly Active Alkaline Phosphatase from the Marine Bacterium Cobetia", Marine Biotechnology, Jun. 2005, pp. 173-178, vol. 7, Springer-Verlag, NE, cited in Extended European Search Report dated Oct. 24, 2014 (6 pages).

*Primary Examiner* — Karen Cochrane Carlson
(74) *Attorney, Agent, or Firm* — Westerman, Hattori, Daniels & Adrian, LLP

(57) ABSTRACT

The present invention provides AP that has a high specific activity and preferably has superior reactivity with respect to various luminescent substrates generally used for high-sensitivity immunoassay analysis. Further preferably, the present invention provides AP having a thermal stability higher than that of CIAP. The alkaline phosphatase of the present invention is derived from the genus *Shewanella* and has the following characteristics: (A) molecular weight: about 104,000; (B) optimum reaction pH: about 9.5; (C) stable pH range: 5.5 to 10.4; (D) thermal stability: 65° C., and (E) specific activity: 5,000 U/mg or more.

11 Claims, 3 Drawing Sheets

ALKALINE PHOSPHATASE

TECHNICAL FIELD

The present invention relates to a bacterial alkaline phosphatase.

BACKGROUND ART

Alkaline phosphatase (EC 3.1.3.1, hereinafter also referred to as AP) is an enzyme that catalyzes a reaction for hydrolyzing phosphoric monoester to generate alcohol and inorganic phosphate, and this enzyme is known for its wide distribution both in procaryotes and eucaryotes. In addition to its use as an enzyme for genetic engineering, AP is widely used as a marker enzyme for enzyme immunoassay analysis (EIA). Currently, calf intestinal AP (CIAP) is predominantly used as AP for EIA. One of the reasons for the convenience of CIAP is its high specific activity. Although the specific activity of commercially available CIAP varies depending on the manufacturer or the grade, some high-specific-activity CIAP with a p-nitro phenyl phosphate substrate has a specific activity of more than 6,000 U/mg protein. In addition, various commercially available high-sensitivity luminescent substrates for CIAP containing 1,2-dioxetane or acridan in their basic structure are conducive to high measurement sensitivity in immunoassay analysis.

One of the most important tasks in immunoassay analysis is to ensure high sensitivity. Although several attempts to achieve high sensitivity have been made, including an attempt to increase the number of marker enzyme molecules adsorbed to each molecule of antigen, and an attempt to develop a high-sensitivity substrate of marker enzymes, the present sensitivity of the immunodiagnosis does not fully meet the required sensitivity level. For example, a negative result obtained by immunodiagnosis using an influenza detection kit does not completely eliminate the possibility of infection. Further, considering that the concentration of the target substance in the specimen is often 1 pM or lower, and considering the reduction in time for diagnosis, increasing the sensitivity is a perpetual challenge.

In order to meet the requirement of high sensitivity, skilled artisans have so far attempted a method of isolating a specific type of CIAP having high specific activity from multiple CIAP isozymes during the process of purification, a method of specifying the gene of CIAP having high specific activity and producing a recombinant enzyme of the gene, and a method of increasing specific activity by introducing an amino acid mutation specific to the site critically involved in the increase in specific activity. On the other hand, there have been no reports so far of successful acquisition of AP having specific activity comparable to or greater than calf-derived AP. Further, although the specific activity of AP has been evaluated based on the reactivity to p-nitro phenyl phosphate, i.e., a substrate of standard AP, AP is actually desired to have high reactivity to various luminescent substrates used in actual high-sensitivity immunoassay analysis. However, there have been no successful reports producing AP superior to CIAP in terms of practical usability from a different source.

CIAP also has a problem of poor stability. Although bacterial AP such as E. coli-derived AP cells has higher stability than that of CIAP, its specific activity is significantly poor compared with CIAP. Non-patent Document 1 and Non-patent Document 2 disclose AP derived from the genus Shewanella as an example of AP having relatively high specific activity. However, the specific activities of the disclosed enzymes were all less than 2,000 U/mg. The AP disclosed in Non-patent Document 1 was patented with the approval of its industrial usability (Patent Document 1). However, the enzyme of that invention is characterized by its usefulness for gene engineering technologies because of its poor thermal stability compared with E. coli-derived AP. Thus, the invention nowhere mentions usability of the enzyme as a marker enzyme for immunoassay analysis, or even a possibility of such usage. Further, although Patent Document 2 discloses AP derived from the genus Bacillus, the specific activity of that enzyme is about 3,000 U/mg, which is not considered sufficient. Further, the Bacillus-derived enzyme has low reactivity with respect to 1,2-dioxetane and acridan luminescent substrates. As such, the Bacillus-derived AP is not sufficiently practical.

CITATION LIST

Patent Documents

Patent Document 1: Japanese Patent No. 3507890
Patent Document 2: Japanese Patent No. 4035738

Non-Patent Document

Non-patent Document 1: Biosci Biotechnol Biochem. 2005 69(2) pp. 364-73. Non-patent Document 2: Biosci Biotechnol Biochem. 2002 66(4) pp. 754-61.

SUMMARY OF INVENTION

Technical Problem

An object of the present invention is to provide an AP having high specific activity, more preferably, also being superior in reactivity with respect to various luminescent substrates used for high-sensitivity immunoassay. More preferably, an object of the present invention is to provide an AP having thermal stability higher than that of CIAP, in addition to the above characteristics.

Technical Solution

As a result of extensive research, the inventors of the present invention discovered an AP from the genus Shewanella having specific activity comparable to that of a high-specific-activity isozyme of CIAP, and high reactivity with respect to a high-sensitivity substrate for AP. The inventors also obtained a gene of this AP, and succeeded in producing a recombinant AP by culturing a microorganism transformed with the gene. The inventors thereby completed the present invention.

Specifically, the present invention has the following aspects.

Item 1. An alkaline phosphatase derived from the genus Shewanella having the characteristics below:
 (A) molecular weight: about 104,000;
 (B) optimum reaction pH: about 9.5;
 (C) stable pH range: 5.5 to 10.4;
 (D) thermal stability: 65° C.; and
 (E) specific activity: 5,000 U/mg or more.
Item 2. An alkaline phosphatase selected from any one of (A) to (C) below:
 (A) an alkaline phosphatase comprising a polypeptide consisting of an amino acid sequence of SEQ ID NO: 2;
 (B) an alkaline phosphatase comprising a polypeptide consisting of the sequence of SEQ ID NO: 2 in which one or more amino acid residues are deleted, substituted, inserted, or added; and (C) an alkaline phosphatase comprising a polypeptide having an identity of 85% or more with the amino acid sequence of SEQ ID NO: 2.

Item 3. A DNA of any one of (A) to (C) below:
- (A) DNA having a nucleotide sequence of SEQ ID NO: 1;
- (B) DNA encoding an amino acid sequence of SEQ ID NO: 2; and
- (C) DNA that hybridizes with the nucleotide sequence of SEQ ID NO: 1 under stringent conditions.

Item 4. A recombinant vector comprising the DNA of Item 3.

Item 5. A transformant obtained by transforming a host cell with the plasmid according to Item 4.

Item 6. The transformant of Item 5, wherein the host cell is *Escherichia coli*.

Item 7. A process for producing the alkaline phosphatase of Item 1 or 2, comprising culturing the transformant of Item 5 or 6, and recovering a protein having an alkaline phosphatase activity from a resulting culture.

Item A1. A polypeptide comprising an amino acid sequence having at least 85% identity to the sequence of SEQ ID NO: 2,
wherein the polypeptide has an alkaline phosphatase activity, and
wherein the polypeptide does not comprise the amino acid sequence of SEQ ID NO: 2.

Item A2. The polypeptide of Item A1, wherein the amino acid sequence having at least 85% identity to the sequence of SEQ ID NO: 2 has at least 90% identity to the sequence of SEQ ID NO: 2.

Item A3. The polypeptide of Item A1, wherein the amino acid sequence having at least 85% identity to the sequence of SEQ ID NO: 2 has at least 95% identity to the sequence of SEQ ID NO: 2.

Item A4. The polypeptide of Item A1, wherein the amino acid sequence having at least 85% identity to the sequence of SEQ ID NO: 2 has at least 98% identity to the sequence of SEQ ID NO: 2.

Item A5. The polypeptide of Item A1, further having at least one of the following characteristics (A) to (E):
- (A) molecular weight: about 104,000;
- (B) optimum reaction pH: about 9.5;
- (C) stable pH range: 5.5 to 10.4;
- (D) thermal stability: 65° C.;
- (E) specific activity: 5,000 U/mg or more.

Item A6. A polypeptide comprising an amino acid sequence having at least 85% identity to the sequence of SEQ ID NO: 2,
wherein the polypeptide has an alkaline phosphatase activity, and
wherein the polypeptide is obtained by recombinantly expressing a DNA encoding a polypeptide having at least 85% identity to the sequence of SEQ ID NO: 2.

Item A7. The polypeptide of Item A6, wherein the recombinant expression of a DNA comprises:
preparing a recombinant vector comprising a DNA encoding a polypeptide having at least 85% identity to the sequence of SEQ ID NO: 2,
introducing the recombinant vector into a cell, and
cultivating the cell.

Item A8. The polypeptide of Item A7, wherein the cell is not *Shewanella* SP T3-3 strain.

Item A9. The polypeptide of Item A7, wherein the cell is at least one cell selected from the group consisting of *Escherichia coli, Bacillus subtilis*, actinomycete, *aspergillus*, yeast, an insect cell, an animal cell, and a plant cell.

Item A10. The polypeptide of Item A6, wherein the amino acid sequence having at least 85% identity to the sequence of SEQ ID NO: 2 has at least 90% identity to the sequence of SEQ ID NO: 2.

Item A11. The polypeptide of Item A6, wherein the amino acid sequence having at least 85% identity to the sequence of SEQ ID NO: 2 has at least 95% identity to the sequence of SEQ ID NO: 2.

Item A12. The polypeptide of Item A6, wherein the amino acid sequence having at least 85% identity to the sequence of SEQ ID NO: 2 has at least 98% identity to the sequence of SEQ ID NO: 2.

Item A13. A DNA comprising a nucleotide sequence having at least 80% identity to the sequence of SEQ ID NO: 1,
wherein the polynucleotide encodes a polypeptide having an alkaline phosphatase activity, and
wherein the DNA does not comprise the sequence of SEQ ID NO: 1.

Item A14. The DNA of Item A13, wherein the nucleotide sequence having at least 90% identity to the sequence of SEQ ID NO: 1 has at least 80% identity to the sequence of SEQ ID NO: 1

Item A15. The DNA of Item A13, wherein the nucleotide sequence having at least 95% identity to the sequence of SEQ ID NO: 1 has at least 90% identity to the sequence of SEQ ID NO: 1.

Item A16. The DNA of Item A13, wherein the codon frequency of the DNA is optimized for expression in a cell other than the genus *Shewanella*.

Item A17. The DNA of Item A16, wherein the cell is at least one cell selected from the group consisting of *Escherichia coli, Bacillus subtilis*, actinomycete, *aspergillus*, yeast, an insect cell, an animal cell, and a plant cell.

Item A18. An expression vector comprising a DNA comprising a nucleotide sequence having at least 80% identity to the sequence of SEQ ID NO: 1,
wherein the polynucleotide encodes a polypeptide having an alkaline phosphatase activity.

Item A19. The expression vector of Item A18, wherein the nucleotide sequence ha at least 90% identity to the sequence of SEQ ID NO: 1.

Item A20. The expression vector of Item A18, wherein the nucleotide sequence has at least 95% identity to the sequence of SEQ ID NO: 1.

Item A21. A polypeptide comprising an amino acid sequence having at least 85% identity to the sequence of SEQ ID NO: 2,
wherein the polypeptide has an alkaline phosphatase activity, and
wherein the polypeptide is bound to at least one substance selected from the group consisting of a nucleic acid probe, biotin, polypeptide, avidin, and antibody.

Item A22. The polypeptide of Item A21, wherein the at least one substance is an antibody.

Item A23. The polypeptide of Item A21, wherein the amino acid sequence having at least 85% identity to the sequence of SEQ ID NO: 2 has at least 90% identity to the sequence of SEQ ID NO: 2.

Item A24. The polypeptide of Item A21, wherein the amino acid sequence having at least 85% identity to the sequence of SEQ ID NO: 2 has at least 95% identity to the sequence of SEQ ID NO: 2.

Item A25. The polypeptide of Item A21, wherein the amino acid sequence having at least 85% identity to the sequence of SEQ ID NO: 2 has at least 98% identity to the sequence of SEQ ID NO: 2.

Effects of Invention

The present invention provides an alkaline phosphatase useful as a marker enzyme for immunoassay, and an alkaline phosphatase-labeled antibody capable of detecting a target substance with high sensitivity.

DESCRIPTION OF EMBODIMENTS

Figure 1:
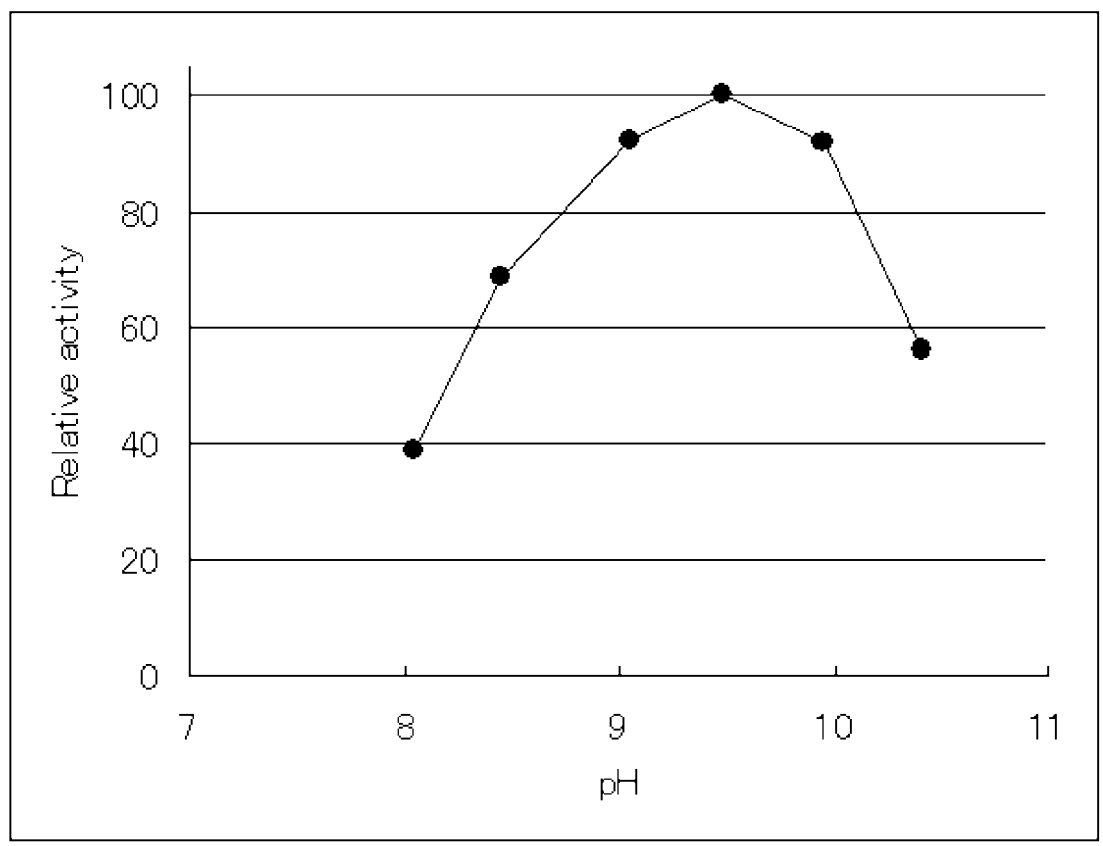
FIG. 1 A graph showing relative activity and reaction pH of AP from *Shewanella* SP T3-3 strain.

The present invention relates to an alkaline phosphatase having high specific activity and high reactivity to luminescent substrates containing 1,2-dioxetane or acridan in their basic structures. The AP of the present invention has the following characteristics:
(A) molecular weight: about 104,000;
(B) optimum reaction pH: about 9.5;
(C) pH stability: 5.5 to 10.4;
(D) thermal stability: 65° C.; and
(E) specific activity: not less than 5,000 U/mg.

The source of the AP of the present invention is not particularly limited insofar as the above characteristics are ensured. However, the AP of the present invention preferably originates from bacterium, and particularly preferably originates from the genus *Shewanella*.

In the present invention, the molecular weight is measured by the following method. 50 µL of AP solution is applied to a TSK-GEL G3000SW (7.5 mm×300 mm; Tosoh Corporation) buffered with a 50 mM phosphate buffer (pH of 6.9, also containing 0.3 M sodium chloride and 0.05% sodium azide), followed by elution at a flow rate of 1 ml/minute using the buffer. The absorbency at 280 nm is monitored, and the elution time is determined from the point where the peak appears. Then the molecular weight is calculated based on a pre-prepared standard curve.

The optimum reaction pH in the present invention is defined as a pH range including a pH value at which the measured AP activity becomes highest. The conditions for the activity measurement other than pH are according to the activity measurement example described later.

The pH stability in the present invention is defined as a remaining activity rate after incubation relative to the activity before incubation, when an AP solution is incubated at 25° C. for 24 hours in a solution containing 0.1 mol/L of a buffer component, 1 mM magnesium chloride, and 0.1 mM zinc sulfate, at a protein concentration of 10 µg/mL. The pH range specified as the pH stability indicates a pH range having a remaining activity rate of not less than 85% under the above conditions. For example, a pH stability of 5.5 to 10.4 means that AP after 24-hour incubation in a buffer with a pH of 5.5 to 10.4 retains at least 85% of the activity compared with before the incubation. In other words, a pH stability of 5.5 to 10.4 means that, when AP is incubated at a predetermined pH for 24 hours, the post-incubation activity of AP is 85% or more as compared to a pre-incubation activity, wherein the pH value falls between a pH of 5.5 to 10.4.

In the present invention, thermal stability refers to a remaining activity rate of AP after heating for 60 minutes an AP solution obtained by dissolving AP in a solution containing 50 mM triethanolamine, 1 mM magnesium chloride, and 0.1 mM zinc sulfate (pH of 7.0) at a protein concentration of 0.01 mg/mL, compared with the AP activity before the heating. The temperature range specified as the thermal stability indicates a temperature range at which the remaining activity rate is not less than 85% under the above conditions. For example, thermal stability of 65° C. means that AP after a 30-minute incubation at a temperature of 65° C. or lower retains activity of at least 85% of the activity before heating. In other words, thermal stability of 65° C. means that, when a 30-minute incubation of AP at a predetermined temperature is performed, 65° C. is the upper limit of the temperature at which the AP activity after the incubation is not less than 85% of the activity before the incubation. The measurement of the activity is performed as follows.

In the present invention, the specific activity is determined by using the method described later in the "Examples of Protein Amount Determination and Specific Activity Calculation" section. The specific activity of the AP of the present invention is at least not less than 5,000 U/mg, further preferably not less than 5,500 U/mg, most preferably not less than 6,000 U/mg. Regarding the specific activity of hitherto-known AP derived from the genus *Shewanella*, Non-patent Document 1 discloses that the specific activity of AP derived from SIB1-strain is 1,880 U/mg at a high temperature (50° C.), and is assumed to be lower at 37° C. Further, for the strain disclosed in Non-patent Document 2, the specific activity is 1,500 U/mg under the conditions of 70° C. and a pH of 10.6, which are the optimum conditions, and is about 1,200 U/mg at 37° C. The AP of the present invention has superior specific activity to that of the known AP derived from the genus *Shewanella*, and thus is clearly distinguished from these AP.

In a preferred embodiment, the present invention is an alkaline phosphatase comprising a polypeptide having an amino acid sequence of SEQ ID NO: 2, or an alkaline phosphatase having a sequence in which one or more amino-acid residues in the amino acid sequence of SEQ ID NO: 2 are deleted, substituted, inserted, or added. The AP may be obtained from a culture solution of the genus *Shewanella* from which the AP is derived, or it may be obtained by introducing a gene into a different host organism from the bacteria from which the AP is derived and expressing the gene in the host organism. When the alkaline phosphatase of the present invention comprises a polypeptide in which one or more amino acids in the amino acid sequence of SEQ ID NO: 2 are substituted, added, deleted, or inserted, the number or the type of the amino acid mutations is not particularly limited insofar as the enzymatic characteristics, such as alkaline phosphatase activity, the aforementioned thermal stability, pH stability, substrate specificity and the like, are ensured. The number of mutations is preferably 1 to 30, more preferably 1 to 15, further preferably 1 to 10, further more preferably 1 to 5, particularly preferably 1 to 3. When the alkaline phosphatase of the present invention comprises a polypeptide in which one or more amino acids in the amino acid sequence of SEQ ID NO: 2 is substituted, the substitution of the amino acid is not limited insofar as the alkaline phosphatase activity or the aforementioned enzymatic characteristics are not impaired. However, the substitution is preferably a replacement of one or more amino acids with one or more similar amino acids. Examples of the similar amino acids include the following amino acids.

Aromatic amino acids: Phe, Trp, Tyr
Aliphatic amino acids: Ala, Leu, Ile, Val
Polar amino acids: Gln, Asn
Basic amino acids: Lys, Arg, His
Acidic amino acids: Glu, Asp
Amino acid having a hydroxy group: Ser, Thr Further, in a preferred embodiment, the present invention is an alkaline phosphatase containing a polypeptide having an identity of 85% or more with the amino acid sequence of SEQ ID NO: 2, more preferably an alkaline phosphatase containing a polypeptide having an identity of 90% or more with the amino acid sequence of SEQ ID NO: 2, further more preferably an alkaline phosphatase containing a polypeptide having an identity of 95% or more with the amino acid sequence of SEQ ID NO: 2, further more preferably an alkaline phosphatase containing a polypeptide having an identity of 98% or more with the amino acid sequence of SEQ ID NO: 2, most preferably an alkaline phosphatase containing a polypeptide having an identity of 99% or more with the amino acid sequence of SEQ ID NO: 2. The term "identity" used herein refers to a proportion of identical amino-acid residues among all overlapping amino acid residues in the optimal alignment when two amino acid sequences are aligned using a known mathematical algorithm in the related technical field. (The algorithm preferably tolerates introduction of a gap in one or both of the sequences for the optimal alignment.)

In a preferred embodiment, the alkaline phosphatase having at least 85% identity to the sequence of SEQ ID NO: 2 preferably does not comprise the amino acid sequence that is identical to the sequence of SEQ ID NO:2 because such an altered alkaline phosphatase may possess an improved characteristic compared to the alkaline phosphatase having the sequence of SEQ ID NO: 2.

In another embodiment, it is preferred that an alkaline phosphatase having at least 85% identity to the sequence of SEQ ID NO: 2 is obtained by recombinantly expressing a DNA encoding polypeptide having at least 85% identity to the sequence of SEQ ID NO:2. The alkaline phosphatase obtained through a recombinant expression of a gene encoding thereof is structurally different from the alkaline phosphatase obtained from Shewanella SP T3-3-strain, for example, with respect to sugar chains bound to the alkaline phosphatase. The difference mainly results from the host cell used for the recombinant expression because the sugar chain pattern is unique to the host cell. In a preferred embodiment, the host cell may be different from Shewanella SP T3-3-strain. A preferred host cell may be a eukaryotic cell. The recombinant expression can be performed according to known methods, examples of which are discussed below.

Examples of the algorithms used to determine the amino acid sequence identity include an algorithm disclosed in Karlin et al., Proc. Natl. Acad. Sci. USA, 90: 5873-5877 (1993). (The algorithm is incorporated in the NBLAST and XBLAST program (version 2.0) (Altschul et al., Nucleic Acids Res., 25: 3389-3402 (1997)).)

According to an amino acid sequence identity search using an identity calculation algorithm of NCBI BLAST (National Center for Biotechnology Information Basic Local Alignment Search Tool), a currently known sequence having the highest identity with the sequence of SEQ ID NO: 2 is a sequence assumed from ORF linked to AP in the genome of Shewanella putrefaciens CN-32-strain. The identity of this sequence with the sequence of SEQ ID NO: 2 is 75%. In other words, no AP having an identity of 80% or more with SEQ ID NO: 2 is known so far. Further, considering that the sequences of the AP derived from the genus Shewanella disclosed in Non-patent Documents 1 and 2 have identities of 67% and 70%, respectively, and that, as described above, the AP of the present invention has a specific activity of more than three times the specific activities of these APs, the AP of the present invention is clearly distinguished from the known AP. One of the standards to define the AP of the present invention is the degree of identity with SEQ ID NO: 2. The identity is preferably at least 85% or more, preferably 90% or more, more preferably 95% or more, further more preferably 98% or more, most preferably 99% or more.

The alkaline phosphatase of the present invention may also be obtained by capturing a microorganism that can produce the enzyme from the environment, and by culturing the microorganism. Further, the alkaline phosphatase of the present invention may also be obtained by introducing the gene encoding the enzyme into a different host and by causing the gene to express in the host.

The AP of the present invention may be appropriately obtained by, for example, (1) a method of extracting AP from cells producing the enzyme and then purifying the AP, (2) a method of chemically synthesizing AP, (3) a method of purifying AP from cells that are caused to express AP through the gene recombinant technology, or (4) a method of biochemically synthesizing AP from a nucleic acid encoding the AP using a cell-free transcription/translation system.

For example, the natural cells for producing the AP of the present invention may be obtained by the following method. First, a sample is obtained from seawater, sand, soil, or the like in a growing environment preferred by various types of the genus Shewanella, such as in an ocean or at an ocean shore. The sample is applied to a versatile bacterial agar culture medium such as an LB agar plate or an M9 glucose plate, and cultured at a temperature of about 25 to 30° C., thereby forming colonies. By screening AP-producing bacteria from the colonies based on the presence of AP activity and analyzing 16SrRNA sequence using a standard method, it is possible to obtain natural cells for producing the AP of the present invention.

The isolation and purification of AP from the natural AP-producing cells or recombinant AP-producing cells is performed, for example, as follows. The AP-producing cells are homogenized in a suitable buffer, and a cell extract is obtained through ultrasonic treatment or a surfactant treatment. Then AP is purified through an appropriate combination of various isolation techniques generally used for protein isolation and purification. Examples of such isolation techniques include, but are not limited to, a method using a difference in solubility, such as salting-out or solvent precipitation; a method using a difference in molecular weight, such as dialysis, ultrafiltration, gel filtration, nondenaturing polyacrylamide gel electrophoresis (PAGE), or sodium dodecyl sulfate-polyacrylamide electrophoresis (SDS-PAGE); a method using an electric charge, such as ion-exchange chromatography or hydroxyapatite chromatography; a method using specific affinity, such as affinity chromatography; a method using a difference in hydrophobicity, such as reversed-phase high-performance liquid chromatography; and a method using a difference in isoelectric point, such as isoelectric point electrophoresis.

The production of AP through chemical synthesis is performed, for example, by synthesizing all or a part of the amino acid sequence of SEQ ID NO: 2 using a peptide synthesis device. Examples of peptide synthesis include solid phase synthesis and liquid phase synthesis. The desired protein can be obtained by connecting a partial peptide or amino acid that constitutes the AP of the present invention with the residual portion by condensation. When the resulting protein contains a protecting group, a step of eliminating a protecting group is further performed. The condensation and the elimination of a protecting group are performed according to methods known per se, such as the methods disclosed in the following Documents (1) and (2).

(1) M. Bodanszky and M. A. Ondetti, Peptide Synthesis, Interscience Publishers, New York (1966)

(2) Schroeder and Luebke, The Peptide, Academic Press, New York (1965)

The AP of the present invention thus obtained may be isolated and purified by a known purification method. Examples of purification methods include solvent extraction, distillation, column chromatography, liquid chromatography, recrystallization, and a combination of these methods. When the resulting AP is a free body, the free body may be converted into an appropriate salt using a known method or a similar method. When the protein is obtained as a salt, the salt may be converted into a different salt using a known method or a similar method.

The AP of the present invention is preferably produced by cloning (or chemically synthesizing) a nucleic acid encoding the protein, and isolating and purifying the protein from a culture product of a transformant containing an expression vector carrying the nucleic acid.

The cloning of the enzyme gene is generally performed as follows. First, the enzyme is completely or partially purified from cells or tissues for producing the desired enzyme, and the amino acid sequence at the N-terminus of the enzyme is obtained using the Edman method or mass analysis. Further, the amino acid sequence of an oligo peptide obtained by partial degradation of the enzyme using a chemical substance or a protease for sequence-specific peptide cleavage is determined in the same manner using the Edman method or mass analysis. Then, a synthetic oligonucleotide having a nucleotide sequence corresponding to the determined partial amino acid sequence is obtained. Using the synthetic oligonucleotide as a probe, DNA encoding the enzyme is cloned by colony (or plaque) hybridization from a cDNA or genomic DNA library prepared from the cells or tissues for producing the enzyme. It is also possible to produce an antibody of the enzyme by a standard method using a part of or the entire fully or partially purified enzyme as an antigen, and DNA encoding the enzyme is closed by an antibody screening method from cDNA or genomic DNA library prepared from the cells or tissues for producing the enzyme. If the gene of an enzyme having a similar enzymological characteristic to the desired enzyme is publicly known, it is possible to access the NCBI BLAST website (http://www.ncbi.nlm.nih.gov/BLAST/), search for a nucleotide sequence similar to the sequence of the known gene, create a probe based on the obtained nucleotide sequence in the above manner, and clone DNA encoding the enzyme using colony (or plaque) hybridization.

Further, the gene may also be directly amplified by polymerase chain reaction (hereinafter referred to as "PCR method") or reverse transcriptase-PCR (hereinafter referred to as "RT-PCR method") by synthesizing a suitable oligonucleotide as a primer based on the nucleotide sequence found through the above search. The PCR is performed using a genomic DNA fraction, the entire RNA, or an mRNA fraction prepared from the AP-producing cells as a template.

The nucleotide sequence of the obtained DNA can be determined according to a known sequence technique, such as the Maxam-Gilberd method or dideoxy termination method.

The gene encoding the AP of the present invention is not particularly limited insofar as the resulting protein satisfies the above characteristics; however, in a preferred embodiment, the gene is DNA having a base sequence encoding an amino acid of SEQ ID NO: 2, more specifically, DNA comprising a nucleotide sequence of SEQ ID NO: 1. Further, insofar as the characteristic of the resulting AP is substantially identical to or superior to the characteristic defined by the present application, the DNA may be a sequence in which one or more bases in the base sequence of SEQ ID NO: 1 are substituted, deleted, added, or inserted. In another embodiment, the DNA includes DNA that hybridizes with the DNA having the nucleotide sequence of SEQ ID NO: 1 under stringent conditions, such as a nucleic acid that encodes a polypeptide having the same property of the polypeptide having an amino acid sequence of SEQ ID NO: 2. Examples of nucleic acids that hybridize with the DNA having the nucleotide sequence of SEQ ID NO: 1 under stringent conditions include a nucleic acid including a base sequence having an identity of 60% or more, preferably 70% or more, more preferably 80% or more, particularly preferably 90% or more, most preferably 95% or more with the base sequence of SEQ ID NO: 1.

In a preferred embodiment, the DNA comprising a nucleotide sequence that has at least 60%, 70%, 80%, 90%, or 95% identity to the sequence of SEQ ID NO: 1 and encodes a polypeptide having alkaline phosphatase activity does not comprise the nucleotide sequence identical to the sequence of SEQ ID NO: 1. Such an altered DNA may encode an alkaline phosphatase with an improved characteristic compared to the alkaline phosphatase having the sequence of SEQ ID NO: 2. The altered DNA may also be preferred because the codon frequency of the DNA may be optimized with respect to the type of a cell within which the DNA is expressed.

The identity of the nucleotide sequence in the present specification can be calculated using an identity calculation algorithm of NCBI BLAST (National Center for Biotechnology Information Basic Local Alignment Search Tool) under the following conditions: anticipated value=10 (with an allowable gap); filtering =ON; match score=1; mismatch score=−3.

The hybridization may be performed according to methods known per se or a similar method, such as a method disclosed in Molecular Cloning, second edition (J. Sambrook et al., Cold Spring Harbor Lab. Press, 1989) or the like. Further, when a commercially available library is used, the hybridization may be performed according to the enclosed user's manual. The hybridization is preferably performed under stringent conditions.

The term "stringent condition" herein refers to a condition in which only the nucleotide sequence having the same transcription termination function as that of the base sequence of SEQ ID NO: 1 forms a hybrid (a specific hybrid) with a nucleotide sequence complementary to SEQ ID NO: 1, and a base sequence that does not have the same transcription termination function as that of the base sequence of SEQ ID NO: 1 does not form a hybrid (a nonspecific hybrid) with a base sequence complementary to SEQ ID NO: 1. A person skilled in the art could easily produce such a condition by changing the temperature during the hybridization reaction or the washing, or by changing the salt concentration, etc., of the hybridization reaction solution and the washing solution. More specifically, an example of a stringent condition of the present invention is a condition in which hybridization is performed at 42° C. in 6×SSC (0.9 M NaCl, 0.09 M trisodium citrate) or 6×SSPE (3 M NaCl, 0.2 M $NaH_2PO_4$, 20 mM EDTA), 2Na, pH of 7.4), followed by washing with 0.5×SSC at 42° C. However, the stringent conditions of the present invention are not limited to this condition. The stringent conditions are preferably highly stringent conditions. A highly stringent condition refers to, for example, a condition in which the washing is performed at 60° C. with a washing solution having a salt concentration corresponding to 0.1× SSC and 0.1% SDS.

As described above, the DNA encoding the AP of the present invention may also be obtained from genomic DNA or RNA (cDNA) of the genus *Shewanella*. It is also possible to construct DNA encoding the entire length of AP by a method of chemically synthesizing a DNA chain, or a method of ligating synthetic oligo DNA short-chains partially overlapping with each other by PCR.

The advantage of the construction of the entire gene length by a combination of chemical synthesis and/or PCR is that it enables designing codons for the entire gene length according to the host to which the gene is introduced. Since the codon usage frequency varies for each biological species, the multiple codons encoding the same amino acid are not evenly used. Genes highly expressed in a biological species usually contain a large number of frequently used codons. Conversely, if the expression amount of a certain gene is low in a biological species, the low expression often derives from infrequently used codons. There are many reports of successful increase in an expression amount of a gene of heterologous protein by substituting the gene sequence with codons frequently used in the living organism. Accordingly, such a modification of codons is expected to increase the expression amount of heterologous genes.

For this reason, DNA encoding the AP of the present invention is preferably modified to codons more suitable for the host cells to which the DNA is introduced (i.e., codons more frequently used in the host organism). The codon usage frequency of a host is defined as a usage frequency of each codon in all the genes in the genome sequence of the host organism. For example, the codon usage frequency is defined based on a usage frequency among 1,000 codons. Further, if the entire genome sequence of the target living organisms is unknown, the codon usage frequency may be found by approximate calculation using the sequences of several major genes. The data of codon usage frequency in the host organism subjected to gene recombination may be obtained from, for example, the genetic code usage frequency database on the website of the Kazusa DNA Research Institute (http://www.kazusa.or.jp). The data of codon usage frequency in the host organism may also be obtained by referring to documents disclosing codon usage frequencies of the various living organisms or performing the calculation of codon usage frequency data of the target host organism. By referring to the obtained data and the gene sequence to be introduced, the codons less frequently used in the genetic sequence of the host organism are substituted with more frequently used codons encoding the same amino acid.

The host cell to which the AP of the present invention is introduced is not particularly limited insofar as a recombinant expression system (described later) is established therein; however, the host cell is preferably a bacterium such as *Escherichia coli* or *Bacillus subtilis*; a microorganism such as actinomycete, *aspergillus* or yeast; an insect cell; an animal cell; or a higher plant. *Escherichia coli* (K12-strain, B-strain, etc.) is particularly preferable. For K12-strain of *Escherichia coli*, examples of frequently used codons include GGT or GGC for Gly, GAA for Glu, GAT for Asp, GTG for Val, GCG for Ala, CGT or CGC for Arg, AGC for Ser, AAA for Lys, ATT or ATC for Ile, ACC for Thr, CTG for Leu, CAG for Gln, and CCG for Pro. An example of such DNA encoding AP replaced with a frequently used codon in the host is DNA that is obtained by replacing DNA encoding genus-*Shewanella*-derived AP with a codon encoding the same amino acid sequence as amino acid sequence of AP, and that is frequently used in K12-strain of *Escherichia coli*.

The present invention also provides a recombinant vector including DNA encoding the AP of the present invention. The recombinant vector of the present invention is not particularly limited insofar as it is capable of replication retention or autonomous proliferation in the various prokaryotic or eukaryotic host cells. Examples thereof include plasmid vectors and virus vectors. The recombinant vector may be simply prepared by ligating the DNA encoding AP with a known cloning or expression vector available in the related technical field using an appropriate restriction endonuclease and ligase, or, if necessary, linker or adapter DNA. Further, it is also possible to use a gene fragment amplified by a DNA polymerase that adds a base to the amplification terminus, such as Taq polymerase. This gene fragment may be ligated to a vector by TA cloning.

Examples of vectors include *Escherichia-coli*-derived plasmids, such as pBR322, pBR325, pUC18, pUC19, pBluescript SK(−), or pBluescript KS(+); yeast-derived plasmids, such as pSH19 or pSH15; and *Bacillus-subtilis*-derived plasmids, such as pUB110, pTP5, or pC194. Further, examples of viruses include bacteriophages such as λphage; papovaviruses such as SV40 or bovine papilloma virus (BPV); retroviruses such as Moloney murine leukemia virus (MoMuLV); and animal and insect viruses such as adenovirus (AdV), adeno-associated virus (AAV), vaccinia virus, or baculovirus.

In particular, the present invention provides an AP expression vector in which the DNA encoding AP is under control of a functional promoter in the target host cells. The vector is not limited insofar as it is a vector that functions in the various prokaryotic or eukaryotic host cells, and has a promoter region that controls the transcription of the downstream gene, and a transcription termination signal, i.e., a terminator region, of the gene, and insofar as the promoter region and the terminator region are connected via a sequence including at least one restriction endonuclease recognition site, more preferably a unique restriction site that cleaves the vector only at the target portion. Examples of the promotor regions include, for host cells derived from *Escherichia coli*, trp promoter, lac promoter, and lecA promoter; for host cells derived from *Bacillus subtilis*, SPO1 promoter, SPO2 promoter, and penP promoter; for host cells derived from yeasts, PHO5 promoter, PGK promoter, GAP promoter, and ADH promoter; for mammalian host cells, virus promoters such as SV40-derived early promoter, MoMuLV-derived long terminal repeat, and adenovirus-derived early promoter. The vector preferably further contains a selectable marker gene for transformant selection (such as genes imparting resistance to drugs such as tetracycline, ampicillin, kanamycin, hygromycin, phosphinothricin, or the like, or genes complementary to an autotrophic mutation). Further, when the DNA encoding AP to be inserted does not contain a start codon or a stop codon, it is preferable to use a vector containing a start codon (ATG or GTG) and a stop codon (TAG, TGA, TAA) in the downstream of the promoter region and the upstream of the terminator region, respectively.

When a bacterium is used as the host cell, generally, the expression vector must include a replicable unit that can undergo autonomous replication in the host cells, in addition to the promoter region and the terminator region. Further, the promoter region includes an operator and a Shine-Dalgarno (SD) sequence in the vicinity of the promoter.

When yeast, an animal cell, or an insect cell is used as the host cell, the expression vector preferably includes an enhancer sequence, untranslated regions at the 5' end and the 3' end of AP mRNA, a polyadenylation site, and the like.

Examples of the host organisms to which the produced recombinant vector is introduced include various cells having a recombinant expression system, including bacteria such as *Escherichia coli* or *Bacillus subtilis*; microorganism hosts such as actinomycete, koji mold, or yeast; insect cells; animal cells; and higher plants. Among these, *Escherichia coli* that is superior in protein expression ability is particularly preferable. The introduction of the recombinant plasmid may be performed by electropolation. For the competent host cells treated with a drug such as calcium chloride, the introduction may be performed by a heat shock method. The transfection of the target recombinant plasmid into a host vector may be selected by searching a microorganism that simultaneously expresses AP activity and a marker, such as various drug-resistant genes, of a vector carrying the target DNA. For example, a microorganism that expresses AP and can be grown in a selected medium for a drug resistance marker is selected.

The AP of the present invention can be produced by culturing the transformant containing an AP-expression vector prepared in the above manner in a culture medium and isolating AP from the obtained culture.

The culture medium preferably contains a carbon source or an inorganic/organic nitrogen source required for the growth of host cells (transformant). Examples of carbon source include glucose, dextran, soluble starch, and sucrose. Examples of inorganic or organic nitrogen sources include ammonium salts, nitrate salts, amino acids, corn steep liquors, peptones, caseins, meat extract soybean cakes, and potato extracts. The culture medium may contain, as desired, other nutrients such as inorganic salts (such as calcium chloride, sodium dihydrogen phosphate, or magnesium chloride), vitamins, or antibiotics (such as tetracycline, neomycin, ampicillin, or kanamycin).

The culture is performed by using any known method in the related field. The culture medium and culture conditions are appropriately selected from the media and conditions below according to the host cells; however, the culture conditions of the present invention are not limited to these media and conditions.

When the host is bacteria, actinomycetes, yeast, filamentous fungi, or the like, for example, liquid culture media containing the above nutritional sources are preferably used. The culture medium preferably has a pH of about 5 to 9. When the host is *Escherichia coli*, preferable culture medium examples include LB culture medium and M9 culture medium (Miller. J., Exp. Mol. Genet, p. 431, Cold Spring Harbor Laboratory, New York (1972)). The culture is generally performed at 14 to 43° C. for about 3 to 72 hours, and if necessary, with ventilation and/or stirring. When the host is *Bacillus subtilis*, the culture is generally performed at 30 to 40° C. for about 16 to 96 hours, and if necessary, with ventilation and/or stirring. When the host is yeast, examples of the culture media include a Burkholder minimum medium (Bostian. K. L. et al, Proc. Natl. Acad. Sci. USA, 77, 4505 (1980)). The culture medium preferably has a pH of about 5 to 8. The culture is generally performed at about 20 to 35° C. for about to 144 hours, and if necessary, with ventilation and/or stirring.

When the host is an animal cell, examples of culture media include minimal essential medium (MEM) (Science, 122, 501 (1952)) containing about 5 to 20% fetal bovine serum, Dulbecco's modified Eagle's culture medium (DMEM) (Virology, 8, 396 (1959)), RPMI1640 culture medium (J. Am. Med. Assoc., 199, 519 (1967)), and 199 culture medium (Proc. Soc. Exp. Biol. Med., 73, 1 (1950)). These culture media may contain a metal salt that stabilizes AP. The metal salt is preferably a magnesium salt and/or a zinc salt. The amount of the metal salt is determined such that the salt does not exhibit toxicity in the culture cells, specifically, the final concentration of magnesium salt is preferably 0.001 mM to 10 mM, and the final concentration of zinc salt is preferably 0.001 mM to 1 mM. However, the amount of metal salt is not limited to these ranges. The culture medium preferably has a pH of about 6 to 8. The culture is generally performed at about 30 to 40° C. for about 15 to 72 hours, and if necessary, with ventilation and/or stirring.

When the host is an insect cell, examples of culture media include a Grace's culture medium (Proc. Natl. Acad. Sci. USA, 82, 8404 (1985)) containing a fetal bovine serum. The culture medium preferably has a pH of about 5 to 8. The culture is generally performed at about 20 to 40° C. for about 15 to 100 hours, and if necessary, with ventilation and/or stirring.

The purification of AP is performed by combining various general isolation techniques according to the fraction having AP activity. AP in the cultured medium may be obtained by centrifuging or filtering the culture to obtain a culture supernatant (filtrate), and isolating AP from the supernatant (filtrate) using an appropriate known isolation technique such as salting-out, solvent precipitation, dialysis, ultrafiltration, gel filtration, nondenaturing PAGE, SDS-PAGE, ion-exchange chromatography, hydroxyapatite chromatography, affinity chromatography, reverse-phase high-performance liquid chromatography, or isoelectric point electrophoresis.

AP in the cytoplasm may be isolated and purified by centrifuging or filtering the culture to collect the cells; suspending the cells in an appropriate buffer; homogenizing (dissolving) the cells and the organelle membrane using, for example, an ultrasonic treatment, a lysozyme treatment, freezing and thawing, osmotic shock, and/or a treatment using a surfactant such as Triton X-100; removing debris by centrifugation or filtration to obtain a soluble fraction; and treating the soluble fraction using the above methods.

A preferable example of a simple and rapid means of obtaining a recombinant AP is a method for adding DNA encoding an amino acid sequence (for example, a sequence of a basic amino acid such as histidine, arginine, or lysine, preferably a sequence of histidine) adsorbable to a metal ion chelate to the portion having the AP coding sequence (preferably N or C terminus) using a genetic engineering technology; expressing the amino acid in the host cell; and isolating AP from an AP activity fraction of the cultured cells using affinity with the carrier on which the metal ion chelate is immobilized. The DNA sequence encoding the amino acid sequence adsorbable to the metal ion chelate may be introduced into the AP coding sequence, for example, through PCR amplification using a hybrid primer obtained by connecting the DNA sequence to a nucleotide sequence encoding the amino acid sequence of C terminus of AP during the step of cloning DNA encoding AP, or through in-frame insertion of DNA encoding AP into an expression vector that includes the DNA sequence before the stop codon. Further, the metal ion chelate adsorbent used for the purification is prepared by bringing a solution containing a transition metal such as bivalent ions of cobalt, copper, nickel and iron, trivalent ions of iron and aluminum, preferably bivalent ion of nickel or cobalt, into contact with a matrix to which a ligand, such as an iminodiacetic acid (IDA) group, a nitrilotriacetic acid (NTA) group, a tris(carboxymethyl)ethylene diamine (TED) group, or the like, is attached, thereby inducing the bond with the ligand. The matrix portion of the chelating adsorbent is not particularly limited insofar as it is a general insoluble carrier.

Alternatively, the purification may be performed through affinity purification using glutation-S-transferase (GST), maltose-binding protein (MBP), HA, FLAG peptide, etc., as a tag.

During the above purification step, membrane condensation, condensation under reduced pressure, and addition of activator and stabilizer may be performed. The solvent used for this step is not particularly limited; however, the solvent is preferably selected from various buffers having a buffering ability at a pH of about 6 to 9, such as K-phosphate buffer, Tris-HCL buffer, Good's buffer, or the like. Further, in order to ensure the stability of AP, a metal salt, preferably a magnesium salt and/or a zinc salt may be added to the buffer. The amount of the metal salt is determined to a range that ensures the AP stabilizing ability of the salt. Specifically, the final concentration of magnesium salt is preferably 0.001 mM to 10 mM, and the final concentration of zinc salt is preferably 0.001 mM to 1 mM. However, the amount of metal salt is not limited to these ranges.

When the resulting AP is a free body, the free body may be converted into a salt by using methods known per se or similar methods. When the obtained AP is a salt, the salt may be converted into a free body or another salt using methods known per se or similar methods.

The purified enzyme may be provided as an industrial material in the liquid form, or may be powdered or granulated. The powderization of the liquid enzyme is performed using an ordinary freeze-drying method.

Further, the AP of the present invention may also be synthesized through in vitro translation using a cell-free protein translation system containing a rabbit reticulocyte lysate, a wheat germ lysate, an *Escherichia coli* lysate, or the like by using RNA corresponding to DNA encoding AP as a template. The RNA encoding the AP of the present invention may be obtained either by purifying mRNA encoding the AP of the present invention from host cells in which RNA is expressed using a standard method, or by preparing cRNA using a cell-free protein translation system containing a RNA polymerase using DNA encoding AP as a template. The cell-free protein transcription/translation system may be obtained from commercially available cell-free protein transcription/translation systems, or may be prepared using methods known per se. For example, an *Escherichia coli* extract may be prepared from the method disclosed in "Transcription and Translation", Pratt J. M. et al., Hames, B. D., and Higgins, S. J., eds., IRL Press, Oxford 179-209 (1984) or the like. Examples of commercially available cell lysates include *Escherichia-coli*-derived cell lysates such as an *E. coli* S30 extract system (Promega Corporation) or an RTS 500 Rapid Translation System (Roche), rabbit-reticulocyte-derived cell lysates such as a Rabbit Reticulocyte Lysate System (Promega Corporation), and wheat-germ-derived cell lysates such as a PROTEIOS™ (Toyobo Co., Ltd.). Among these, wheat-germ-derived cell lysates are preferable. Wheat-germ-derived cell lysates can be produced, for example, using the method disclosed in Johnston F. B. et al., Nature, 179: 160-161 (1957) or Erickson A. H. et al., Meth. Enzymol., 96: 38-50 (1996).

Examples of the systems or devices for protein synthesis include a batch method (Pratt, J. M. et al. (1984) (mentioned above)), a continuous cell-free protein synthesis system (Spirin A. S. et al., Science, 242: 1162-1164 (1988)) for continuously providing an amino acid, an energy source, etc., to a reaction system, dialysis method (Kigawa et al., 21st Molecular Biology Society of Japan, WIDE), and a superposition method (PROTEIOS™ Wheat germ cell-free protein synthesis core kit user's manual: Toyobo Co., Ltd.). It is also possible to use a method of supplying template RNA, amino acid, an energy source, and the like to a synthetic reaction system as necessary, and discharging a synthesized product or a degradation product as necessary (JP2000-333673A).

Another embodiment of the present invention is a conjugate labeled with the above alkaline phosphatase. The substance to be labeled is appropriately selected from, for example, biological substances such as a nucleic acid probe or biotin; and proteins such as a polypeptide, avidin, or antibody. The labeling may be performed using a maleimide method, pyridyl disulfide method, or glutaraldehyde method. When the AP of the present invention is expressed in a eukaryotic host, a periodic acid method using the sugar chain on the AP surface may be performed. A suitable labeling method may be selected according to the substance to be labeled, the functional group to be used, the target usage, etc. The details of the production methods for an AP-labeled antibody or AP-labeled antigen used for ELISA or immunodiagnosis reagent, and the methods for immunoassay analysis using the antibody or antigen are disclosed, for example, in "Ultra-sensitivity Enzyme Immunoassay Analysis" (Eiji ISHIKAWA, Gakkai Shuppan Center Co., Ltd).

A typical immunoassay analysis is performed as follows. First, a solution containing a primary antibody of the target substance is supplied and caused to be adsorbed to a solid phase by incubation. The solid phase may be a container to be used as a reaction layer or may be separately prepared magnetic beads. After the primary antibody is adsorbed, the solution is removed. After rinsing it several times with a washing buffer, a non-adsorbed substance is removed. A washing buffer is selected from those exhibiting a buffering ability at a pH around neutral, at which the antibody can be stably present. The washing buffer may contain a surfactant to improve the washing ability. The washed solid phase is immersed in a liquid containing a protein such as bovine blood serum albumin or deactivating type AP, and subjected to incubation for blocking nonspecific binding. Thereafter, the solid phase is washed with the above washing buffer, and then brought into contact with the target sample (measurement sample), followed by incubation for a predetermined time, thereby causing the measurement sample to be adsorbed into the primary antibody. Then the sample solution is completely removed, the solid phase is washed with the above washing buffer, and a solution containing an AP-labeled secondary antibody is added. Incubation is performed for a predetermined time so that the AP-labeled secondary antibody is adsorbed to the measurement object captured by the primary antibody in the solid phase. Then the solution is completely removed, the solid phase is washed with the aforementioned washing buffer, and an AP substrate is added for activity detection. Examples of AP substrates include p-nitro phenyl phosphate and 5-bromo-4-chloro-3-indolyl phosphate when the activity is detected by a colorimetric method, 4-methylumbelliferyl phosphate when the activity is detected by a fluorescence method, and 1,2-dioxetane or acridan luminescent substrate and like various luminescent substrates when the activity is detected by a luminescence method. Among these, the AP of the present invention is particularly superior in reactivity to luminescent substrates; thus, methods using a luminescent substrate are preferable. Examples of luminescent substrates include, but are not limited to, AMPPD, CSPD, CDP-star, Lumigen PPD, Lumi-Phos530, and APS-5. The measurement of the measurement sample substance is performed according to a standard curve plotted using a standard solution of the measurement sample substance.

A typical immunoassay analysis reagent kit includes a reaction layer, a solid phase that contains an immobilized primary antibody and is blocked with a protein such as a bovine blood serum albumin or deactivating type AP, a standard solution of the target antigen, an AP-labeled secondary antibody, a washing solution used for the washing the sample or the secondary antibody after the reaction in the reaction layer, an AP substrate solution, and a user's manual. Examples of AP substrate include p-nitro phenyl phosphate and 5-bromo-4-chloro-3-indolyl phosphate when the activity is detected by a colorimetric method, 4-methylumbelliferyl phosphate when the activity is detected by a fluorescence method, and 1,2-dioxetane or acridan luminescent substrate and like various luminescent substrate when the activity is detected by a luminescence method. Among these, the AP of the present invention is particularly superior in reactivity to luminescent substrates; thus, methods using a luminescent substrate are preferable. Examples of luminescent substrates include, but are not limited to, AMPPD, CSPD, CDP-star, Lumigen PPD, Lumi-Phos530, and APS-5.

Example of Activity Measurement

Unless otherwise specified, the AP activity of the present invention is measured as follows. First, Solutions A and B are prepared in the following manner.
A: 1 M diethanolamine buffer (pH of 9.8)
B: 0.67 M p-nitro phenyl phosphate (dissolved in Solution A)
2.9 ml of Solution A and 0.1 ml of Solution B are prepared in a cuvette (optical path length=1.0 cm), and pre-heated at 37° C. for 5 minutes. 0.1 ml of AP solution is added and gently mixed. Changes in absorbency at 405 nm were recorded for 3 to 5 minutes using a spectrophotometer adjusted to 37° C. based on water. Referring to the linear portion, a change in absorbency per minute is determined (AOD test). For a blind trial, 0.1 ml of a buffer containing an enzyme dissolved therein is added instead of an enzyme, and a change in absorbency per minute is determined in the same manner (AOD blank). Based on the obtained values, the AP activity is determined by the following equation.

AP activity (U/ml)={(ΔOD test−ΔOD blank)×3.1}/{18.2×1.0×0.1}

3.1: Amount of reaction liquid (ml) after addition of AP solution
18.2: Millimolar extinction coefficient (cm$^2$/μmol) of p-nitro phenol under the above measurement conditions
1.0: Optical path length (cm)
0.1: Addition amount (ml) of enzyme solution Examples of Protein Amount Determination and Specific Activity Calculation The protein amount of the present invention is calculated according to a measured absorbency at 280 nm. More specifically, an enzyme solution is diluted with distilled water so that the absorbency at 280 nm falls within a range of 0.1 to 1.0, and the absorbency at 280 nm (Abs) is measured with an absorption spectrometer adjusted to the zero point using distilled water. The protein concentration of the present invention is approximately in the relation of 1 Abs≈1 mg/ml, and obtained by multiplying the result by the measured absorbency and the dilution factor of the measured solution. Further, the specific activity of the present invention refers to AP activity (U/mg) per mg of a protein amount measured by the above method. The AP activity is found by the method described above in the "Example of Activity Measurement" section.

The present invention is more specifically explained below with reference to Examples. However, the present invention is not limited to these examples.

Example 1

Preparation of AP-Producing Strain

A sand sample obtained from seawater in the gulf of Suruga (Suruga-shi, Fukui Prefecture) was applied on an LB agar medium (pH of 7.5) containing 50 μg/ml 5-bromo-4-chloro-3-indolyl phosphate (BCIP), and cultured at 25° C. Among the colonies formed on the culture medium, the blue-colored colonies resulting from hydrolysis of phosphoric ester in BCIP were refined. The resulting strain was subjected to colony direct PCR using 10F/800R primers disclosed in "Rapid Identification of Microorganisms Based on Molecular Biological Method" (Japanese Pharmacopoeia), thereby amplifying a part of the DNA region of the 16SrRNA sequence. As a result of an NCBI-BLAST search, the sequence was assumed to be a bacterium of the genus *Shewanella*. Accordingly, the strain was named "*Shewanella* sp. T3-3-strain."

Example 2

Cloning of AP Gene

*Shewanella* sp. T3-3-strain was inoculated in a 5-ml LB culture medium in a test tube and cultured with shaking for 24 hours at 30° C. The culture solution was placed in a 1.5-ml Eppendorf tube and subjected to centrifugation with a refrigerated centrifuge for 5 minutes at 12,000 rpm. The resulting supernatant was removed by suction to obtain a bacterial cell. Genomic DNA was obtained from the cells using a genomic DNA extraction kit (NPK-1; Toyobo Co., Ltd.) according to the user's manual attached to the kit. The obtained genomic DNA was digested with restriction endonuclease BamHI or BglII, and purified using a DNA purification kit (NPK-6: Toyobo Co., Ltd.). After the purification, the restriction endonuclease was removed. The DNA fragment was mixed with BamHI-digested and purified pBR322. A ligation liquid (Ligation High: Toyobo Co., Ltd.) in the same amount as that of the mixed solution was added and the mixture was incubated overnight at 16° C. The ligation solution was added to *Escherichia coli* JM109-strain competent cells (Competent high JM109; Toyobo Co., Ltd.), and the plasmid was transformed by a heat-shock treatment, thereby producing a genomic DNA library of the T3-3-strain. The obtained library was inoculated on a LB agar culture medium containing 50 μg/ml of BCIP and 100 μg/ml of ampicillin, and cultured at 30° C., thereby forming transformed colonies. Among the colonies, blue-colored colonies were picked with a toothpick, inoculated on a 5-ml LB culture medium (containing 100 μg/ml ampicillin) in a test tube, and cultured with shaking for 16 hours at 30° C. A plasmid (pBRT3-3LPP) containing AP gene derived from T3-3-strain was extracted from the culture solution using a plasmid extraction kit (NPK-3; Toyobo Co., Ltd.), and the plasmid was purified. The resulting plasmid had an insertion of about 6 kb. This sequence was subjected to sequence analysis to determine the sequence of the entire length of the AP gene and the neighboring region. The determined nucleotide sequence of the AP gene and the amino acid sequence assumed from the nucleotide sequence are shown in SEQ ID NO: 1 and SEQ ID NO: 2, respectively.

Example 3

Expression of AP in *Escherichia-coli*-Derived Host

A primer having a sequence including the entire length of the AP gene and the promoter region of the AP gene of T3-3-strain, as well as a BamHI site at each 5' end, (SEQ ID NOs: 3 and 4) was produced. Using this primer, PCR was performed using a plasmid (pBRT3-3LPP) as a template. The amplified DNA fragment was applied to TAE gel containing 1% agarose and subjected to electrophoresis. Under UV irradiation, the band of the amplified fragment was cleaved, and extraction and purification of DNA from the gel were performed using a DNA purification kit (NPK-6). The genomic DNA fragment was digested with restriction endonuclease BamHI and ligated with pBluescprSK(−) treated with the same restriction endonuclease, thereby producing an expression plasmid (pBST3-3LPP1). The ligated plasmid was introduced into an *Escherichia coli* C600-strain through electropolation, applied to an LB agar culture medium containing 100 µg/ml ampicillin, and cultured overnight at 30° C., thereby forming transformed colonies. A loopful of the transformed colony was inoculated on a 60-ml LB culture medium (containing 100 µg/ml ampicillin) in a 500-ml Sakaguchi flask, and cultured with shaking overnight at 30° C. and 180 rpm. The entire culture solution was supplied to a 6-L production culture medium (1.2% peptone, 2.4% yeast extract, 0.1% NaCl, 0.1 mM zinc sulfate, 100 µg/ml ampicillin, pH of 7.0) in a 10-L jar fermenter, and cultured for 48 hours at 30° C. with ventilation at 2 L/minute and stirring at 380 rpm. As a result, 800 U/ml AP was produced.

Example 4

Purification of *Escherichia Coli* Recombinant AP 500 ml of the culture solution obtained in Example 3 was dispensed into centrifuge tubes and centrifuged for 30 minutes at 8,000 rpm using a high-speed refrigerated centrifuge device, and the supernatant was decanted off to collect bacterial cells. The bacterial cells were suspended in 1.5 L of 20 mM Tris-HCL buffer (pH of 7.5), and homogenized at a pressure of 80 MPa with a French press homogenizer. 5% (w/v) polyethylenimine was added to the homogenized liquid in an amount of 3%, and the generated solid was removed after settling by centrifugation for minutes at 8,000 rpm using a high-speed refrigerated centrifuge device. 0.15-saturated ammonium sulfate was dissolved in the liquid, and the generated solid was removed by centrifugation for 30 minutes at 8,000 rpm using a high-speed refrigerated centrifuge device. Ammonium sulfate was further added and dissolved so that the final concentration was 0.55 saturated, and the mixture was centrifuged for 30 minutes at 8,000 rpm using a high-speed refrigerated centrifuge device. The supernatant was decanted off to collect a precipitate containing AP. 90 ml of 20 mM Tris-HCL buffer (pH of 7.5, containing 1 mM magnesium chloride) was added to the precipitate to dissolve the precipitate. The resulting solution was desalted using G-25 Sepharose gel (GE Healthcare) buffered with 20 mM Tris-HCL buffer (pH of 7.5, containing 1 mM magnesium chloride). The resulting solution was adsorbed to a DEAE Sepharose gel (GE Healthcare) buffered with 20 mM Tris-HCL buffer (pH of 7.5, containing 1 mM magnesium chloride), and subjected to gradient elution by increasing the NaCl concentration to 0.5 M with the buffer. Fractions having AP activity were collected and ammonium sulfate was dissolved to 0.05 saturation. The solution was applied to Octyl Sepharose gel (GE Healthcare) buffered with 20 mM Tris-HCL buffer (pH of 7.5, containing 0.05-saturated ammonium sulfate and 1 mM magnesium chloride), and the buffer was kept running through it, thereby isolating non-adsorbed fractions. More ammonium sulfate was added and dissolved in this solution so that the final concentration was 0.2 saturation, and the solution was applied to Phenyl Sepharose gel (GE Healthcare) buffered with 20 mM Tris-HCL buffer (pH of 7.5, containing 0.2-saturated ammonium sulfate and 1 mM magnesium chloride), and subjected to gradient elution by decreasing the ammonium sulfate concentration to zero using the buffer. The fractions containing AP were collected and desalted with G-25 Sepharose gel buffered with a 20 mM triethanolamine (pH of 7.5, containing 1 mM magnesium chloride and 0.1 mM zinc sulfate), thereby obtaining purified T3-3-strain-derived recombinant AP. The specific activity of the AP solution was measured and found to be 6090 U/mg.

Example 5

Measurement of Molecular Weight of T3-3-Strain-Derived Recombinant AP by Gel Filtration 50 µL of the AP solution obtained in Example 4 was applied to a TSK-GEL G3000SW (7.5 mm×300 mm; Tosoh Corporation) buffered with a 50 mM phosphate buffer (pH of 6.9, also containing 0.3 M sodium chloride and 0.05% sodium azide), followed by elution at a flow rate of 1 ml/minute using the buffer. The absorbency at 280 nm was monitored, and the elution time was determined from on the point where the peak appears. The molecular weight was calculated based on a pre-prepared standard curve. The molecular weight of AP was estimated to be about 104,000.

Example 6 pH Stability of T3-3-Strain-Derived Recombinant AP

The AP produced in Example 4 was diluted with various buffers having a pH of 4 to 12 to a concentration of 10 µg/ml, and incubated at 25° C. for 24 hours. The AP activities before and after the incubation were compared for each solution, thereby calculating remaining activity rates. FIG. 1 shows the relationship between pH and remaining activity rate. The buffers used were acetic acid having a pH of 4.0 to 5.5, MES having a pH of 5.5 to 6.5, triethanolamine having a pH of 6.5 to 9.5, and glycine having a pH of 9.7 to 11.6. The concentrations of these buffers were all 50 mM. The AP had a remaining activity rate of 85% or more at a pH range of 5.5 to 10.4.

Example 7

Optimum Reaction pH of Recombinant AP Derived from T3-3-Strain

Figure 2:
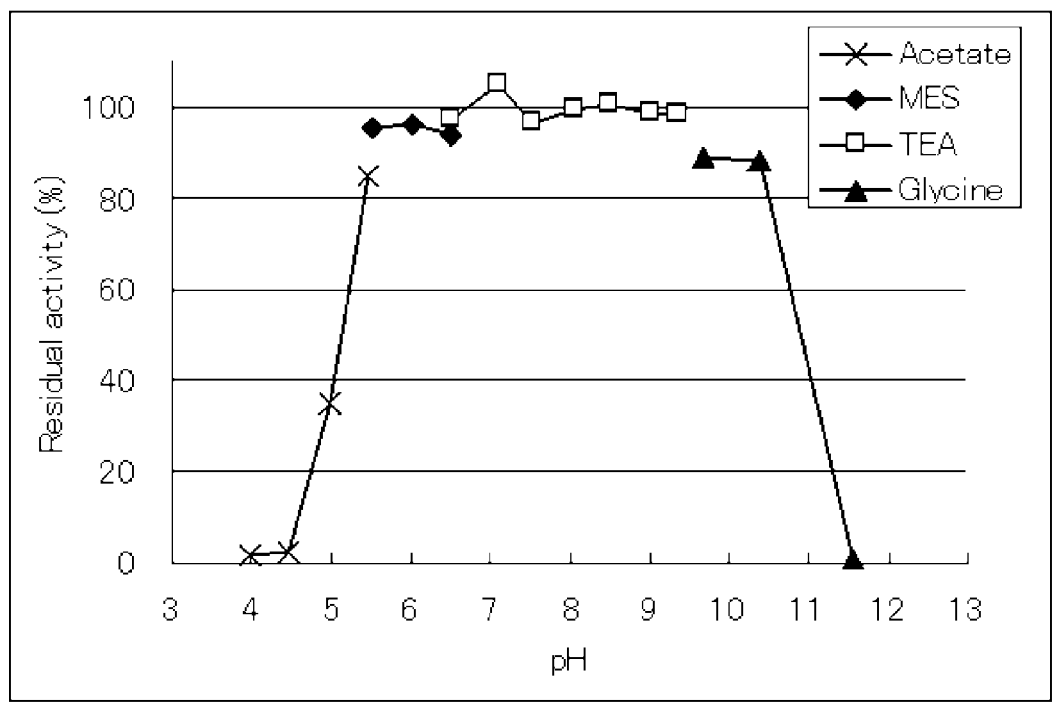
FIG. 2 A graph showing stability of AP from *Shewanella* SP T3-3 strain at different pH levels.

Six reaction mixtures with different pH values were prepared by changing the pH of Buffer A used above in the "Example of Activity Measurement" section in increments of 0.5 from 8.0 to 10.5. The measurement used above in the "Example of Activity Measurement" section was performed using these six reaction mixtures. FIG. 2 shows the results. FIG. 2 indicates relative activities referring to the highest activity at measured pH conditions as 100. The activity was highest at a pH of 9.5. Thus it was revealed that the optimum pH falls in a range of more than 9.25 but less than 9.75.

Example 8

Thermal Stability of T3-3-Strain-Derived Recombinant AP

Figure 3:
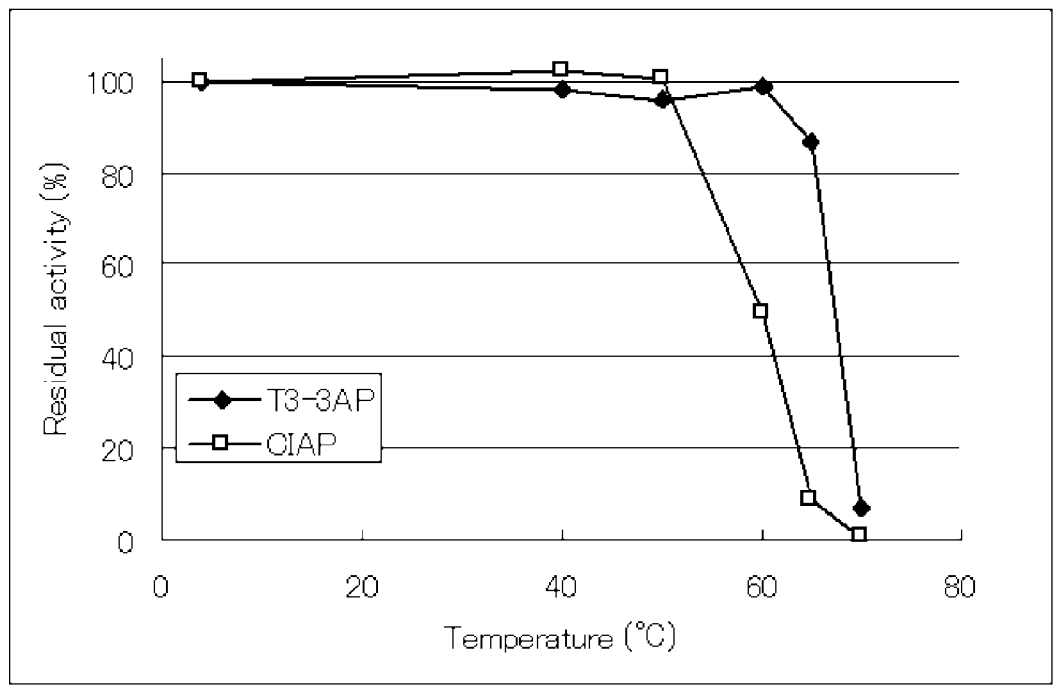
FIG. 3 A graph showing stabilities of AP from *Shewanella* SP T3-3 strain and CIAP at different temperatures.

The AP produced in Example 4 was diluted with 50 mM triethanolamine, 1 mM magnesium chloride, and 0.1 mM zinc sulfate (pH of 7.0) to a concentration of 10 μg/ml. The solution was divided into 6 portions, and each was incubated for 60 minutes at a temperature of 25° C., 40° C., 50° C., 60° C., 65° C., or 70° C. The AP activities before and after the incubation were compared for each solution. Further, as a control, the same treatment was performed for CIAP having a specific activity of 6,000 U/mg. FIG. 3 shows the incubation temperatures and the remaining activity rates after the incubation. The AP of the present invention maintained an activity of 87% even at 65° C. In contrast, the remaining activity rates of CIAP were 49% at 60° C. and 8% at 65° C. This shows that the thermal stability of the AP of the present invention is superior to that of CIAP.

Example 9

Comparison of Reactivity to AP Luminescent Substrate

The AP obtained in Example 4 and, as a control, AP derived from calf small intestine (specific activity of 6,000 U/mg) were diluted with a 20 mM phosphate potassium buffer (pH of 7.5, containing 1 mM magnesium chloride) to a concentration of 0.5 U/ml or 0.05 U/ml. Each of the AP diluents thus obtained was supplied to a 96-well ELISA plate in an amount of to 5 μL per well. 50 μL each of AMPPD, APS-5, Lumi-Phos 530, and CDP-star were added thereto as luminescent substrates. The luminescence intensity was measured using a multilabel plate counter (Wallac 1420 ARVO MX; PerkinElmer Co., Ltd.). Table 1 shows luminescence intensities relative to an intensity of 100. An intensity of 100 is a value obtained when each substrate is reacted with CIAP. For each substrate, T3-3-strain-derived AP exhibited a superior sensitivity to that of CIAP.

TABLE 1

| Substrate | Relative activity | |
|---|---|---|
| | CIAP | T3-3-strain-derived AP |
| AMPPD | 100 | 270 |
| Lumi-Phos 530 | 100 | 174 |
| CDP-star | 100 | 284 |
| APS-5 | 100 | 845 |

Example 10

Production of AP-Labeled Mouse Anti-Human CRP Antibody 2 mg of the AP obtained in Example 4 was diluted with 50 mM sodium borate, 1 mM magnesium chloride, and 0.1 mM zinc chloride (pH of 7.6) so that the volume became 0.5 ml. The diluent was placed in a cellophane tube and dialyzed overnight at 4° C. using the same buffer. 10 μL of N-succinimidyl-6-maleimidehexanoate solution (0.17 mg dissolved in 10 μL of N,N-dimethyl formamide) was added to the dialysis liquid, and the mixture was incubated for 30 minutes at 30° C. The resulting mixture was applied to a 5-ml G-25 fast-flow prepacked column (GE Healthcare) buffered with a 0.1 M Tris-HCL buffer (pH of 7.0, containing 1 mM magnesium chloride and 0.1 mM zinc sulfate), and subjected to buffer substitution by feeding the buffer and collecting protein fractions. The amount of the maleimide group introduced into the maleimide-bound AP was determined according to the method disclosed in "Ultra-sensitivity Enzyme Immunoassay Analysis" (Eiji ISHIKAWA, Gakkai Shuppan Center Co., Ltd). The results showed that, on average, 5.0 maleimide groups were introduced per AP molecule.

50 μL of 0.1 M 2-mercaptoethylamine was added and mixed with a mouse anti-human CRP antibody (IgG) buffered with 0.1 M phosphate sodium buffer (pH of 6.0) at a concentration of 2 mg/0.45 ml. The mixture was incubated for 90 minutes at 37° C., thereby producing reduced IgG. Then, buffer substitution was performed with the same buffer by using a 5-ml G-25 fast-flow prepacked column (GE Healthcare) buffered with a 0.1 M phosphate sodium buffer (pH of 6.0) containing 5 mM ethylenediamine tetra acetic acid.

Equivalent amounts of the reduced IgG solution and the maleimide-bound AP solution were mixed, and incubated for 20 hours at 4° C., thereby producing a conjugate. This solution was subjected to gel filtration using a TSK gel G3000SW (Tosoh Corporation) buffered with a 10 mM Tris-HCL buffer, 0.1 M sodium chloride, 1 mM magnesium chloride, and 0.1 mM zinc chloride (pH of 6.8). Fractions containing AP-labeled mouse anti-human CRP antibody were isolated based on the AP activity and absorbency at 280 nm.

Example 11

Immunoassay Analysis Using AP-Labeled Mouse Anti-Human CRP Antibody

A solution containing a mouse anti-human CRP antibody obtained from a clone different from that used in Example 10 was added to a 96-well ELISA plate in an amount of 50 μL per well. The liquid was spread over the bottom of the well by shaking, and incubated for 2 hours at 25° C. The liquid was then completely removed. PBS+0.05% Tween 20 (pH of 7.4) was added in an amount of 300 μL per well, and the liquid was removed. This treatment was performed three times to complete the washing step. Thereafter, PBS+0.1% bovine blood serum albumin was added in an amount of 300 μL per well, and the plate was blocked by incubation for an hour at 25° C. The liquid was then completely removed. Then PBS+0.05% Tween 20 (pH of 7.4) was added in an amount of 300 μL per well, and the liquid was removed. This treatment was performed three times to complete the washing step, thereby obtaining an anti-human CRP antibody-coated ELISA plate. A solution containing $10^{-6}$ to $10^{-1}$ mg/dl recombinant human CRP (rCRP, Oriental Yeast Co., Ltd.) was added to the plate in an amount of 50 μL per well. The liquid was spread over the bottom of the well by shaking, and incubated for 1 hour at 37° C. so that the antigens were captured by the primary antibodies on the solid phase. The liquid was then completely removed. PBS+0.05% Tween 20 (pH of 7.4) was added in an amount of 300 μL per well, and the liquid was removed. This treatment was performed three times to remove free antigens. An AP-labeled mouse anti-human CRP antibody (0.4 μg/ml solution) obtained in Example 10 was added in an amount of 50 μL per well.

Figure 4:
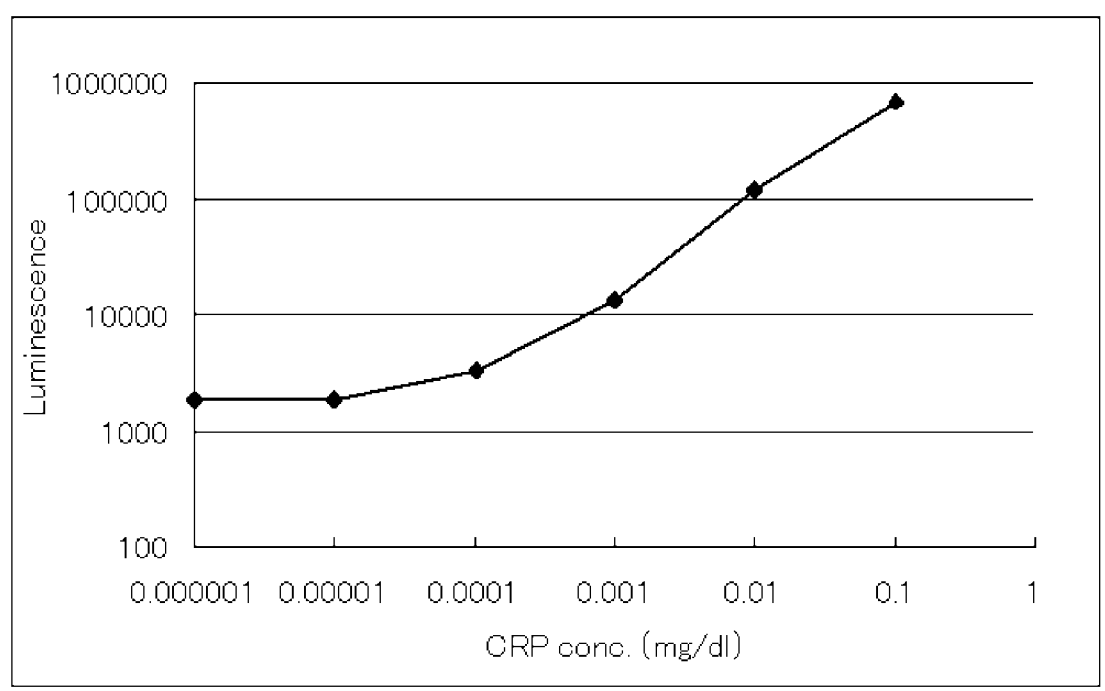
FIG. 4 A graph showing a standard curve obtained by sandwich ELISA using a *Shewanella* SP T3-3-strain AP-labeled antihuman CRP antibody and a recombinant human CRP.

The liquid was spread over the bottom of the well by shaking, and incubated for 1 hour at 37° C., thereby incorporating the antigens to the conjugates. The liquid was then completely removed. PBS+0.05% Tween 20 (pH of 7.4) was added in an amount of 300 μL per well, and the liquid was removed. This treatment was performed three times to remove free conjugates. Lumi-Phos 530 (Lumigen) subjected to light-shielded heating at 37° C. in advance was added in an amount of 50 μL per well. The luminescence for each well was measured using a multilabel plate counter (Wallac 1420 ARVO MX; PerkinElmer Co., Ltd.), and a standard curve was plotted (FIG. 4). It was revealed that using the AP-labeled conjugate of the present invention makes it possible to measure the amount of target antigen.

INDUSTRIAL APPLICABILITY

The alkaline phosphatase of the present invention is useful as a marker enzyme for immunoassay analysis and also as a marker enzyme for probe hybridization or western blotting. The alkaline phosphatase of the present invention may also be used as a gene engineering enzyme for dephosphorylation of DNA fragments.

The invention claimed is:

1. A polypeptide comprising an amino acid sequence having at least 90% identity to the sequence of SEQ ID NO: 2,
   wherein the polypeptide has an alkaline phosphatase activity, and
   wherein the polypeptide does not comprise the amino acid sequence of SEQ ID NO: 2.

2. The polypeptide of claim 1, wherein the amino acid sequence having at least 90% identity to the sequence of SEQ ID NO: 2 has at least 95% identity to the sequence of SEQ ID NO: 2.

3. The polypeptide of claim 1, wherein the amino acid sequence having at least 90% identity to the sequence of SEQ ID NO: 2 has at least 98% identity to the sequence of SEQ ID NO: 2.

4. The polypeptide of claim 1, further having at least one of the following characteristics (A) to (E):
   (A) molecular weight: about 104,000;
   (B) optimum reaction pH: about 9.5;
   (C) stable pH range: 5.5 to 10.4;
   (D) thermal stability: 65° C.;
   (E) specific activity: 5,000 U/mg or more.

5. A polypeptide comprising an amino acid sequence having at least 85% identity to the sequence of SEQ ID NO: 2,
   wherein the polypeptide has an alkaline phosphatase activity, and
   wherein the polypeptide is bound to at least one substance selected from the group consisting of a nucleic acid probe, biotin, polypeptide, avidin, and antibody.

6. The polypeptide of claim 5, wherein the at least one substance is an antibody.

7. The polypeptide of claim 5, wherein the amino acid sequence having at least 85% identity to the sequence of SEQ ID NO: 2 has at least 90% identity to the sequence of SEQ ID NO: 2.

8. The polypeptide of claim 5, wherein the amino acid sequence having at least 85% identity to the sequence of SEQ ID NO: 2 has at least 95% identity to the sequence of SEQ ID NO: 2.

9. The polypeptide of claim 5, wherein the amino acid sequence having at least 85% identity to the sequence of SEQ ID NO: 2 has at least 98% identity to the sequence of SEQ ID NO: 2.

10. The polypeptide of claim 5, wherein the polypeptide does not comprise the amino acid sequence of SEQ ID NO: 2.

11. The polypeptide of claim 5, further having at least one of the following characteristics (A) to (E):
    (A) molecular weight: about 104,000;
    (B) optimum reaction pH: about 9.5;
    (C) stable pH range: 5.5 to 10.4;
    (D) thermal stability: 65° C.;
    (E) specific activity: 5,000 U/mg or more.

* * * * *

```
                           SEQUENCE LISTING

<160> NUMBER OF SEQ ID NOS: 4

<210> SEQ ID NO 1
<211> LENGTH: 1332
<212> TYPE: DNA
<213> ORGANISM: Shewanella sp. T3-3

<400> SEQUENCE: 1
atgagcgtca ccaaaacatc actcttattg ctgactatcg gattagtatt ttcagctagc      60
agcaaggccg cacccgagct tgaaaacggg cctatgaaac cgccatcaaa acctaaaaac     120
atcgttatta tggtgggtga cggcatgggc ccttcgtaca ccagcgccta ccgctatttc     180
aaagataatc ctgacaccga agaagtcgaa caaaccgtat tcgatagact cttagttggc     240
atggcaagta cgtatcctgc cagtgtcagc ggctatgtca cagattctgc tgcggcggca     300
actgcgctcg ccacaggcgt aaaatcttat aatggcgcta tttccgtcga tacccaaaag     360
caacacttac caaccatgct cgaaaaagcc aaagcattag ggttaagcac aggtgtggcg     420
gtaacatcac aaatcaacca tgccacgccc gcggcatttt tagcccacaa cgagagccgt     480
aaaaattacg atgctctggc gctcagttat ttagacacaa atgccgatgt acttttgggc     540
ggcggacaga agtatttctc gcctgaactg ctcgaaaaat tcaccgccaa aggttatcaa     600
cacattagcc gctttgaaga tttggccact ataacccaac ccaaagtcat tggcctgttt     660
gcacaggtgc aactgccttg ggcgctcgat gagaaaaatg caaatcgcct cagcactatg     720
actcaaaaag ccctcgattt actctcacaa aatgagcaag gctttgtatt gttagtcgaa     780
ggcagcttga ttgactgggc cggacacagc aatgatatcg ccaacaccat gggcgaaatg     840
gatgaatttg ccaatgcact cgaagtggtt gagcagtttg tacgccaaca tccagacacc     900
ttaatggtag ccactgccga tcataatacc ggtgcactct caattggtgc tggcggagat     960
tatcgctgga acccagagat tttacgcaat atgtctgcca gcacggacac gcttgcctta    1020
gccgcactcg gtggtgacca atggcaagcc gatctggccc gaggtttagg atttgagcta    1080
aacgccgatg aagtgactca attgagcaca gcccgaatgc aaggtcttga accatgact     1140 gaagccattc gtaaaatcat cgacaagcgc accggcactg gctggacaac ctcaggccac    1200
actggcacag acgtacaagt atttgccgca ggccctgctg ccgagttatt taatggccac    1260
caagataata ccgacatagc caacaaaatt ttcactttat tgcctaaacc gaaaaaagcc    1320
aaaaccgaat aa                                                        1332

<210> SEQ ID NO 2
<211> LENGTH: 443
<212> TYPE: PRT
<213> ORGANISM: Shewanella sp. T3-3

<400> SEQUENCE: 2

Met Ser Val Thr Lys Thr Ser Leu Leu Leu Thr Ile Gly Leu Val
1               5                  10                  15

Phe Ser Ala Ser Ser Lys Ala Ala Pro Glu Leu Glu Asn Gly Pro Met
                20                  25                  30

Lys Pro Pro Ser Lys Pro Lys Asn Ile Val Ile Met Val Gly Asp Gly
            35                  40                  45
```

```
Met Gly Pro Ser Tyr Thr Ser Ala Tyr Arg Tyr Phe Lys Asp Asn Pro
 50                  55                  60
Asp Thr Glu Glu Val Glu Gln Thr Val Phe Asp Arg Leu Leu Val Gly
 65                  70                  75                  80
Met Ala Ser Thr Tyr Pro Ala Ser Val Ser Gly Tyr Val Thr Asp Ser
                 85                  90                  95
Ala Ala Ala Ala Thr Ala Leu Ala Thr Gly Val Lys Ser Tyr Asn Gly
            100                 105                 110
Ala Ile Ser Val Asp Thr Gln Lys Gln His Leu Pro Thr Met Leu Glu
        115                 120                 125
Lys Ala Lys Ala Leu Gly Leu Ser Thr Gly Val Ala Val Thr Ser Gln
130                 135                 140
Ile Asn His Ala Thr Pro Ala Ala Phe Leu Ala His Asn Glu Ser Arg
145                 150                 155                 160
Lys Asn Tyr Asp Ala Leu Ala Leu Ser Tyr Leu Asp Thr Asn Ala Asp
                165                 170                 175
Val Leu Leu Gly Gly Gly Gln Lys Tyr Phe Ser Pro Glu Leu Leu Glu
            180                 185                 190
Lys Phe Thr Ala Lys Gly Tyr Gln His Ile Ser Arg Phe Glu Asp Leu
        195                 200                 205
Ala Thr Ile Thr Gln Pro Lys Val Ile Gly Leu Phe Ala Gln Val Gln
210                 215                 220
Leu Pro Trp Ala Leu Asp Glu Lys Asn Ala Asn Arg Leu Ser Thr Met
225                 230                 235                 240
Thr Gln Lys Ala Leu Asp Leu Leu Ser Gln Asn Glu Gln Gly Phe Val
                245                 250                 255
Leu Leu Val Glu Gly Ser Leu Ile Asp Trp Ala Gly His Ser Asn Asp
            260                 265                 270
Ile Ala Asn Thr Met Gly Glu Met Asp Glu Phe Ala Asn Ala Leu Glu
        275                 280                 285
Val Val Glu Gln Phe Val Arg Gln His Pro Asp Thr Leu Met Val Ala
290                 295                 300
Thr Ala Asp His Asn Thr Gly Gly Leu Ser Ile Gly Ala Gly Gly Asp
305                 310                 315                 320
Tyr Arg Trp Asn Pro Glu Ile Leu Arg Asn Met Ser Ala Ser Thr Asp
                325                 330                 335
Thr Leu Ala Leu Ala Ala Leu Gly Gly Asp Gln Trp Gln Ala Asp Leu
            340                 345                 350
Ala Arg Gly Leu Gly Phe Glu Leu Asn Ala Asp Glu Val Thr Gln Leu
        355                 360                 365
Ser Thr Ala Arg Met Gln Gly Leu Glu Thr Met Thr Glu Ala Ile Arg
370                 375                 380
Lys Ile Ile Asp Lys Arg Thr Gly Thr Gly Trp Thr Thr Ser Gly His
385                 390                 395                 400
Thr Gly Thr Asp Val Gln Val Phe Ala Ala Gly Pro Ala Ala Glu Leu
                405                 410                 415
Phe Asn Gly His Gln Asp Asn Thr Asp Ile Ala Asn Lys Ile Phe Thr
            420                 425                 430
Leu Leu Pro Lys Pro Lys Lys Ala Lys Thr Glu
        435                 440

<210> SEQ ID NO 3
<211> LENGTH: 40
<212> TYPE: DNA
```

```
<213> ORGANISM: Artificial
<220> FEATURE:
<223> OTHER INFORMATION: Artificial Sequence oligonucleotide

<400> SEQUENCE: 3
aaaagatctc agcatcacta aaagtattat ccacatgatg                           40

<210> SEQ ID NO 4
<211> LENGTH: 40
<212> TYPE: DNA
<213> ORGANISM: Artificial
<220> FEATURE:
<223> OTHER INFORMATION: Artificial Sequence oligonucleotide

<400> SEQUENCE: 4
aaaagatctt gtgttggcgc cgataaacat aagtggcgtg                           40
```